United States Patent [19]

Mahan

[11] Patent Number: 4,588,721

[45] Date of Patent: May 13, 1986

[54] TREATMENT OF NEGATIVE SYMPTOMS OF SCHIZOPHRENIA

[75] Inventor: Donald R. Mahan, San Jose, Calif.

[73] Assignee: The Upjohn Company, Kalamazoo, Mich.

[21] Appl. No.: 674,616

[22] Filed: Nov. 26, 1984

Related U.S. Application Data

[63] Continuation-in-part of Ser. No. 531,552, Sep. 12, 1983, abandoned.

[51] Int. Cl.[4] .............................................. A61K 31/41
[52] U.S. Cl. ..................................................... 514/220
[58] Field of Search ................................. 514/359, 220

[56] References Cited

U.S. PATENT DOCUMENTS 3,907,820  9/1975  Meguro et al. ..................... 260/308
3,987,052  10/1976  Hester, Jr. .......................... 260/239
4,116,956  9/1978  Meguro et al. ..................... 260/230

FOREIGN PATENT DOCUMENTS 1331015  9/1973  United Kingdom .

OTHER PUBLICATIONS

Lingjaerde, "Benzodiazepines in the Treatment of Schizophrenia", *The Benzodiazepines : From Molecular Biology to Clinical Practice*, Raven Press, New York, (1983), pp. 369–381.
Lingjaerde, Acta Psychiat. Scand. 65: 339–354, (1982).
*Amer. Jr. of Psychiatry*, vol. 139, No. 3, Mar. 1982, pp. 297–302, "Ventricular Enlargement in Schizophrenia: Relationship to Positive and Negative Symptoms" by N. C. Andreasen, et al.
*Arch. Gen. Psychiatry*, vol. 39, Jul. 1982, pp. 789–794. "Negative v. Positive Schizophrenia" by Andreasen and Olsen.
*Comprehensive Psychiatry*, vol. 7, No. 6, Dec. 1966, pp. 488–493, "Therapeutic Studies in Therapy Resistant Schizophrenic Patients" by T. M. Itil, et al.
*British Medical Journal*, Jan. 12, 1980, pp. 66–68, "Molecular Pathology of Schizophrenia: More than One Disease Process?" by T. J. Crow.
*British Jr. Psychiatry*, vol. 137, (1980), pp. 379–386, "Positive and Negative Schizophrenic Symptoms and the Role of Dopamine" by A. V. P. Mackay.
*Arch. Gen. Psychiatry*, vol. 36, Nov. 1979, pp. 1325–1330, "Thought, Language and Communication Disorders" by N. C. Andreasen.
*Amer. Jr. of Psychiatry*, vol. 136, No. 7, Jul. 1979, pp. 944–947, "Affective Flattening and the Criteria for Schizophrenia", by N. C. Andreasen.
Siris, Samuel G., et al, "Drug Treatment of Acute Schizophrenia", Schizophrenia and Affective Disorders, edited by A. Rifkin, John Wright PSG, Inc., (1983) pp. 237–280.

*Primary Examiner*—Stanley J. Friedman
*Attorney, Agent, or Firm*—William G. Jameson

[57] ABSTRACT

Therapeutic process for treating the negative symptoms of schizophrenia in humans comprising the systematic administration of a compound of the formula

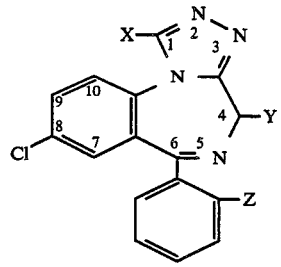

Formula I X is a member selected from the group consisting of —H, —CH$_3$, and —CH$_2$—O—R;
wherein R is hydrogen, alkyl of from 1 to 3 carbon atoms, inclusive,

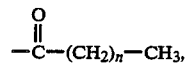

or

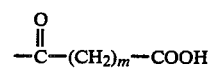

wherein n is 0 to 16, inclusive, and m is 1 to 16 inclusive;
Y is hydrogen or, provided when Z is hydrogen and X is CH$_3$, hydroxy;
Z is hydrogen or, provided when Y is hydrogen and X is —CH$_3$, chloro;
including the N-oxides and pharmacologically acceptable acid addition salts thereof in combination with a pharmaceutical carrier.

18 Claims, No Drawings

TREATMENT OF NEGATIVE SYMPTOMS OF SCHIZOPHRENIA

CROSS REFERENCE TO RELATED APPLICATION

This application is a continuation-in-part of application Ser. No. 531,552 filed Sept. 12, 1983, now abandoned.

BRIEF SUMMARY OF THE INVENTION

This invention is a prophylatic or therapeutic process for treating the negative symptoms of schizophrenia in humans comprising the systemic administration of a benzodiazepine of the Formula I:

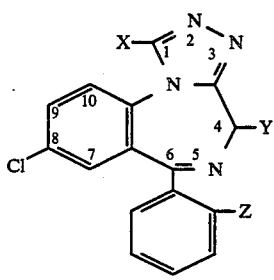

Formula I

X is a member selected from the group consisting —H, —CH$_3$ and —CH$_2$—O—R;
wherein R is hydrogen, alkyl of from 1 to 3 carbon atoms, inclusive

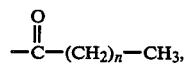

or

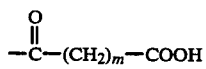

wherein n is 0 to 16, inclusive, and m is 1 to 16, inclusive;

Y is hydrogen or, provided when Z is hydrogen and X is CH$_3$, hydroxy;

Z is hydrogen or, provided when Y is hydrogen and X is —CH$_3$, chloro;

and including the N-oxides and pharmacologically acceptable acid addition salts thereof in combination with a pharmaceutical carrier.

BACKGROUND OF THE INVENTION

When Kraepelin first identified the disorder that he called "dementia praecox," he was referring to a syndrome similar to the dementias of later life but beginning at a relatively early age. Since that time, several changes have occurred in the concept of schizophrenia. In stressing the importance of "fundamental symptoms" and minimizing the importance of a deteriorating course, Bleuler broadened the concept of schizophrenia to include milder cases. Some investigators have added a requirement of "clear consciousness," usually defined as intact orientation and memory. A distinction between organic and functional psychoses has been embedded in our nomenclature during recent decades, also serving to preclude conceptualizing schizophrenia as organic in origin (see the Diagnostic and Statistical Manual of Mental Disorders, 3rd edition). Finally, during recent years investigators have emphasized the importance of "positive" symptoms, such as delusions and hallucinations, in the definition of schizophrenia, primarily because they are easy to identify and define reliably. The increased interest in positive symptoms has led to a deemphasis of the importance of more 'negative' symptoms, such as affective flattening or impoverished thinking, which are similar to those occurring in typical dementias. Andreasen, et al. Am. J. Psychiatry 139:3 March 1982, 297–301. Diagnostic criteria for distinguishing positive schizophrenia and negative schizophrenia is disclosed by Andreasen and Olsen, *Arch Gen Psychiatry* Vol. 39, p. 789–794 July 1982.

The use of adinazolam, 8-chloro-1-[(dimethylamino)-methyl]-6-phenyl-4H-s-triazolo[4,3-a][1,4]benzodiazepine, in the treatment of schizophrenia, primarily for the negative symptoms of schizophrenia is the prior invention of another. The use of adinazolam and some other 1-(nitrogen-containing group) triazolobenzodiazepines and their pharmacologically acceptable salts for treating psychosis and schizophrenia is disclosed in U.S. Pat. No. 4,472,397.

O. Lingjaerde concludes in "Effect of the Benzodiazepine Derivative Estazolam in patients with Auditory Hallucinations. A Multicentre Double-Blind, Cross-Over Study", *Acta Psychiat. Scand.* 65:339–354 (1982) that estazolam (as an addition to neuroleptics) had a significantly better effect than placebo on the global clinical state, on the frequency of, and attitude towards the hallucinations, and also on the single symptoms "compulsive thoughts" and "visual hallucinations" (items in the Comprehensive Psychopathological Rating Scale). Professor Lingjaerde also reported at p. 353:

"In a recent survey of the literature (Lingjaerde (1982) it is concluded that a therapeutic effect in schizophrenia has been demonstrated in controlled trials for at least four benzodiazepines: chlorodiazepoxide, diazepam, alprazolam, and estazolam, but most other benzodiazepines have not been given adequate trial."

However, according to Lingjaerde the reference to alprazolam is an error and should have been lorazepam. In fact, Professor Lingjaerde stated in a letter in August of 1984 that he had never seen any paper on the possible effect of alprazolam in schizophrenia—such a study would seem well worth performing, considering the similarity between alprazolam and estazolam.

The citation "Lingjaerde (1982): 'Benzodiazepines in the Treatment of Schizophrenia' (in press)" in *Acta Psychiat. Scand.* 65:339–354 (1982) was published as an article in the book The Benzodiazepines: From Molecular Biology to Clinical Practice, edited by E. Costa, Raven Press, New York, pp. 369–381 (LC Number QV 77.9 34792 1981) and contains the same error at p. 377 regarding alprazolam instead of lorazepam.

In a review article entitled "Drug Treatment of Acute Schizophrenia", pp. 237–280 in *Schizophrenia and Affective Disorders*, edited by A. Rifkin, John Wright.PSG, Inc. (1983), Siris S. G. et al reported:

"To date, double-blind studies, with one exception, have not shown benzodiazepines to be effective in schizophrenia. The exception is the study of Kellner and associates. Using a model of intensive design, they studied three patients who were repeatedly switched from chlorodiazepoxide to placebo, while an antipsychotic drug was continued . . . ".

The compounds of Formula I have been variously indicated for the management of anxiety disorders, sedative, tranquilizer, muscle relaxant and anti-depressant activity.

DETAILED DESCRIPTION

The compounds of Formula I can be prepared by methods disclosed in U.S. Pat. No. 3,987,052, issued Oct. 19, 1976; U.S. Pat. No. 4,116,956, issued Sept. 26, 1978; U.S. Pat. No. 3,987,052, issued Oct. 19, 1976, U.S. Pat. No. 3,907,820, issued Sept. 23, 1975; and Belgium Pat. No. 782,680 or French Pat. No. 7215118 and as disclosed hereafter.

The oxidation of a compound of the Formula I normally follows a 2-step process with the formation of an oxazirino structure.

The (5) N-oxides of a compound of the Formula I can also be made by reacting a 2-methoxy-5-phenyl-7-chloro-3H-1,4-benzodiazepine 4-oxide with acethydrazide. This reaction can be carried out in a solvent inert to the reaction such as a lower alkanol of boiling range of about 100° C. or above, especially 1-butanol or 1-pentanol. It is convenient to reflux the reaction mixture, and a convenient reaction temperature is in the range of 100°-140° C. Under these conditions, the reaction time will be from 12 to 48 hours.

The peracid oxidation method described above for producing the (5) N-oxides of a compound of the Formula I produces an intermediate oxazirino compound as described above, and this latter compound can be further rearranged to the desired (5) N-oxide by heating in an appropriate solvent inert to the reaction and capable of being sustained in liquid form at normal pressures at temperatures of 150°-200° C. Suitable reaction solvents are the liquid paraffinic hydrocarbons of 10-18 carbon atoms or other solvent hydrocarbons boiling above about 150° C. such as mesitylene. The reaction is conveniently carried out under reflux for 10 minutes to 1 hour.

Acid addition salts of compounds of the Formula I can be prepared by neutralization of the free base with the appropriate amount of an inorganic or organic acid, examples of which are hydrochloric, hydrobromic, sulfuric, nitric, phosphoric, acetic, lactic, benzoic, salicyclic, glycolic, succinic, tartaric, maleic, malic, pamoic, cyclohexanesulfamic, citric and methanesulfonic acids, and like acids. The neutralization can be carried out by a variety of procedures known to the art to be generally useful for the preparation of amine acid addition salts. The choice of the most suitable procedure will depend on a variety of factors including convenience of operation, economic consideration, and particularly the solubility characteristics of the particular free base, the acid, and the acid addition salt. If the acid is soluble in water, the free base can be dissolved in water containing an equivalent amount of the acid, and thereafter, the water can be removed by evaporation; in some instances, the salt precipitates from the aqueous solution, particularly when cooled, and evaporation is not necessary. If the acid is soluble in a relatively nonpolar solvent, for example, diethyl ether or diisopropyl ether, separate solutions of acid and free base in such a solvent can be mixed in equivalent amounts, whereupon the acid addition salt will usually precipitate because of its relatively low solubility in the nonpolar solvent. Alternatively, the free base can be mixed with an equivalent amount of the acid in the presence of a solvent of moderate polarity, for example, a lower alkanol, a lower alkanone, or a loweralkyl ester of a lower alkanoic acid. Examples of these solvents are ethanol, acetone, and ethyl acetate, respectively. Subsequent admixture of the resulting solution of acid addition salt with a solvent of relatively low polarity, for example, diethyl ether or hexane, will usually cause precipitation of the acid addition salt. These acid addition salts are useful for upgrading the free bases.

The compositions of the present invention are presented for administration to humans in unit dosage forms, such as tablets, capsules, pills, powders, granules, sterile parenteral solutions or suspensions, and oral solutions or suspensions, and oil in water and water in oil emulsions containing suitable quantities of the compound of Formula I.

For oral administration either solid or fluid unit dosage forms can be prepared. For preparing solid compositions such as tablets, the compound of Formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Wafers are prepared in the same manner as tablets, differing only in shape and the inclusion of sucrose or other sweetener and flavor. In their simplest embodiment, capsules, like tablets, are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The term unit dosage form as used in the specification and claims refers to physically discrete units suitable as unitary dosages for human subjects and animals, each unit containing a predetermined quantity of a active material calculated to treat the negative symptoms of schizophrenia in association with the required pharmaceutical diluent, carrier or vehicle. The specifications for the novel unit dosage forms of this invention are dictated by and directly dependent on (a) the unique characteristics of the active material and the particular effect to be achieved, and (b) the limitations inherent in the art of compounding such an active material for use in humans and animals, as disclosed in detail in this specification, these being features of the present invention. Examples of suitable unit dosage forms in accord with this invention are tablets, capsules, pills, suppositories, powder packets, granules, wafers, cachets, teaspoonfuls, tablespoonfuls, dropperfuls, ampuls, vials, segregated multiples of any of the foregoing, and other forms as herein described.

The dosage of the compound for treatment depends on route of administration; the age, weight, and condition of the patient and the particular compound.

When X is —H or —CH$_3$ a dosage schedule of from about 1 to 10 mg/day in a single or divided dose, embraces the effective range for treating the negative symptoms of schizophrenia for which the compositions are effective. The dosage to be administered is calculated on the basis of from about 0.01 to about 0.4 mg/kg by weight of subject per day. Generally, depending upon the conditions of concern to the prescribing physician, a dosage schedule of from about 5 to 10 milligrams/day in divided doses, preferably about 5 to 8 milligrams/day in divided doses, is the usual effective range of alprazolam, 8-chloro-1-methyl-6-phenyl-4H-s-triazolo[4,3-a][1,4]benzodiazepine, for treating the negative symptoms of schizophrenia in adult patients of average body weight. During the initial period of therapy, a starting dose of about 2 to 3 milligrams/day of alprazolam in divided doses (1 mg two or three times a day) is utilized for the first one or two days and then the dose is gradually increased to about 5 to about 10 mg/day (preferably about 5 to about 8 mg/day) over a 7 to 10 day period.

In order to minimize possible sedation, it is generally desirable to prescribe a larger portion of the daily dose of alprazolam or other compound of Formula I at bedtime and to take the other doses with a meal/snack, e.g. a 5 mg/day dose is administered to provide 1 mg at 7:00 a.m. and 3:00 p.m. and 3 mg at 11:00 p.m., a 6 mg/day dosage is administered to provide 1 mg a 7:00 a.m., 2 mg at 3:00 p.m., and 4 mg at 11:00 p.m., a 9 mg/day dosage is administered to provide 3 mg at 7:00 a.m., 3.00 p.m. and 11:00 p.m., and a 10 mg/day dosage is administered to provide a 3 mg at 7:00 a.m. and 3:00 p.m. and 4 mg at 11:00 p.m. It is, of course, well-recognized that the daily dose can be formulated in a sustained release tablet or other dosage form, utilizing, for example, hydroxypropylmethyl cellulose or other cellulose ethers as disclosed in U.S. Pat. No. 3,065,143, if desired, to provide for a once or twice a day administration schedule.

When X is —CH$_2$—O—R a dosage schedule of from about 2 to 20 mg/day in a single or divided dose, embraces the effective range for treating the negative symptoms of schizophrenia for which the compositions are effective. The dosage to be administered is calculated on the basis of from about 0.02 to about 0.8 mg/kg by weight of subject.

The compound is compounded with a suitable pharmaceutical carrier in unit dosage form for convenient and effective administration. In the preferred embodiments of this invention, the dosage units contain the compound in: 0.1, 0.5, 1, 5, 10, 20 and 50 mg amounts for systemic treatment; and 0.1% to 1% w/v for parenteral treatment.

The compositions are useful in preventing and treating the negative symptoms of schizophrenia, i.e. the compositions can be administered to schizophrenic patients exhibiting negative symptoms.

The following examples are illustrative of the best mode contemplated by the inventor for carrying out his invention and are not to be construed as limiting.

EXAMPLE 1

A lot of 10,000 tablets, each containing 0.5 mg of 8-chloro-6-phenyl-4H-s-triazolo[4,3-a][1,4]benzodiazepine is prepared from the following types and amounts of ingredients:

| | |
|---|---|
| 8-Chloro-6-phenyl-4H—s-triazolo-[4,3-a][1,4]benzodiazepine | 1 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in treating the negative symptoms of schizophrenia at a dose of 1 tablet 4 times a day.

EXAMPLE 2

One thousand two-piece hard gelatin capsules, each containing 0.5 mg of 8-chloro-6-phenyl-4H-s-triazolo[4,3-a][1,4]benzodiazepine are prepared from the following types and amounts of ingredients:

| | |
|---|---|
| 8-Chloro-6-phenyl-4H—s-triazolo-[4,3-a][1,4]benzodiazepine | 0.5 Gm |
| Talc | 25 Gm |
| Magnesium stearate | 250 Gm |

The ingredients are mixed well and filled into capsules of the proper size.

Capsules so prepared are useful to treat the negative symptoms of schizophrenia at a dose of one capsule four times a day.

EXAMPLE 3

One thousand tablets for sublinqual use are prepared from the following ingredients:

| | |
|---|---|
| 8-Chloro-6-phenyl-4H—s-triazolo-[4,3-a][1,4]benzodiazepine | 1 Gm |
| Polyethylene glycol 4,000, powdered | 150 Gm |
| Polyethylene glycol 6,000, powdered | 75 Gm |

The ingredients are mixed well and compressed into sublingual-type tablets weighing 226 mg.

These tablets placed under the tongue are useful in treating the negative symptoms of schizophrenia at a dose of 1 tablet.

EXAMPLE 4

Soft gelatin capsules for oral use, each containing 10 mg of 8-chloro-6-phenyl-4H-s-triazolo[4,3-a][1,4]benzodiazepine are prepared by first dispersing the micronized compound in corn oil to render the material capsulatable and then encapsulating in the usual manner.

One capsule taken daily is useful to treat the negative symptoms of schizophrenia.

EXAMPLE 5

One thousand tablets, each containing 5 mg. of 8-chloro-6-phenyl-4H-s-triazolo[4,3-a][1,4]benzodiazepine are made from the following types and amounts of ingredients:

| | |
|---|---|
| 8-Chloro-6-phenyl-4H—s-triazolo-[4,3-a][1,4]benzodiazepine | 5 Gm |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to treat the negative symptoms of schizophrenia at a dose of one tablet twice a day.

EXAMPLE 6

A sterile preparation suitable for intramuscular injection and containing 1 mg of 8-chloro-6-phenyl-4H-s-triazolo[4,3-a][1,4]benzodiazepine in each milliliter is prepared from the following ingredients:

| | |
|---|---|
| 8-Chloro-6-phenyl-4H—s-triazolo-[4,3-a][1,4]benzodiazepine | 1 Gm |
| Benzyl benzoate | 200 ml |
| Methylparaben | 1.5 Gm |
| Propylparaben | 0.5 Gm |
| Cottonseed oil, q.s. | 1,000 ml |

One milliliter of this sterile preparation is injected to treat the negative symptoms of schizophrenia.

EXAMPLE 7

A lot of 10,000 tablets, each containing 0.5 mg of 8-chloro-1-methyl-4-hydroxy-6-phenyl-4H-s-triazolo[4,3-a][1,4]benzodiazepine methanesulfonate is prepared from the following types and amounts of ingredients:

| | |
|---|---|
| 8-Chloro-1-methyl-4-hydroxy-6-phenyl-4H—s-triazolo-[4,3-a][1,4]benzodiazepine methanesulfonate | 1 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in treating the negative symptoms of schizophrenia at a dose of 1 tablet 4 times a day.

EXAMPLE 8

One thousand two-piece hard gelatin capsules, each containing 0.5 mg of 8-chloro-1-methyl-4-hydroxy-6-phenyl-4H-s-triazolo[4,3-a][1,4]-benzodiazepine methanesulfonate are prepared from the following types and amounts of ingredients:

| | |
|---|---|
| 8-Chloro-1-methyl-4-hydroxy-6-phenyl-4H—s-triazolo[[4,3-a][1,4]benzodiazepine methanesulfonate | 0.5 Gm |
| Talc | 25 Gm |
| Magnesium stearate | 250 Gm |

The ingredients are mixed well and filled into capsules of the proper size.

Capsules so prepared are useful to treat the negative symptoms of schizophrenia at a dose of one capsule four times a day.

EXAMPLE 9

One thousand tablets for sublinqual use are prepared from the following ingredients:

| | |
|---|---|
| 8-Chloro-1-methyl-4-hydroxy-6-phenyl-4H—s-triazolo[[4,3-a][1,4]benzodiazepine methanesulfonate | 1 Gm |
| Polyethylene glycol 4,000, powdered | 150 Gm |
| Polyethylene glycol 6,000, powdered | 75 Gm |

The ingredients are mixed well and compressed into sublingual-type tablets weighing 245 mg.

These tablets placed under the tongue are useful in treating the negative symptoms of schizophrenia at a dose of 1 tablet.

EXAMPLE 10

Soft gelatin capsules for oral use, each containing 10 mg of 8-chloro-1-methyl-4-hydroxy-6-phenyl-4H-s-triazolo[[4,3-a][1,4]benzodiazepine methanesulfonate are prepared by first dispersing the micronized compound in corn oil to render the material capsulatable and then encapsulating in the usual manner.

One capsule taken daily is useful to treat the negative symptoms of schizophrenia.

EXAMPLE 11

One thousand tablets, each containing 5 mg of 8-chloro-1-methyl-4-hydroxy-6-phenyl-4H-s-triazolo[[4,3-a][1,4]benzodiazepine methanesulfonate are made from the following types and amounts of ingredients:

| | |
|---|---|
| 8-Chloro-1-methyl-4-hydroxy-6-phenyl-4H—s-triazolo[[4,3-a][1,4]benzodiazepine methanesulfonate | 5 Gm |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to treat the negative symptoms of schizophrenia at a dose of one tablet twice a day.

EXAMPLE 12

A sterile preparation suitable for intramuscular injection and containing 1 mg of 8-chloro-1-methyl-4-hydroxy-6-phenyl-4H-s-triazolo-[4,3-a][1,4]benzodiazepine methanesulfonate in each milliliter is prepared from the following ingredients:

| | |
|---|---|
| 8-Chloro-1-methyl-4-hydroxy-6-phenyl-4H—s-triazolo[[4,3-a][1,4]benzodiazepine methanesulfonate | 1 Gm |
| Benzyl benzoate | 200 ml |
| Methylparaben | 1.5 Gm |
| Propylparaben | 0.5 Gm |
| Cottonseed oil, q.s. | 1,000 ml |

One milliliter of this sterile preparation is injected to treat the negative symptoms of schizophrenia.

EXAMPLE 13

A lot of 10,000 tablets, each containing 0.5 mg of 8-chloro-1-methyl-6-phenyl-4H-s-triazolo[4,3-a][1,4]benzodiazepine is prepared from the following types and amounts of ingredients:

| | |
|---|---|
| 8-Chloro-1-methyl-6-phenyl-4H—s-triazolo[4,3-a][1,4]benzodiazepine | 1 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in treating the negative symptoms of schizophrenia at a dose of 1 tablet 4 times a day.

EXAMPLE 14

One thousand two-piece hard gelatin capsules, each containing 0.5 mg of 8-chloro-1-methyl-6-phenyl-4H-s-triazolo[4,3-a][1,4]benzodiazepine are prepared from the following types and amounts of ingredients:

| | |
|---|---|
| 8-Chloro-1-methyl-6-phenyl-4H—s-triazolo[4,3-a][1,4]benzodiazepine | 0.5 Gm |
| Talc | 25 Gm |
| Magnesium stearate | 250 Gm |

The ingredients are mixed well and filled into capsules of the proper size.

Capsules so prepared are useful to treat the negative symptoms of schizophrenia at a dose of one capsule four times a day.

EXAMPLE 15

One thousand tablets for sublinqual use are prepared from the following ingredients:

| | |
|---|---|
| 8-Chloro-1-methyl-6-phenyl-4H—s-triazolo[4,3-a][1,4]benzodiazepine | 1 Gm |
| Polyethylene glycol 4,000, powdered | 150 Gm |
| Polyethylene glycol 6,000, powdered | 75 Gm |

The ingredients are mixed well and compressed into sublingual-type tablets weighing 226 mg.

These tablets placed under the tongue are useful in treating the negative symptoms of schizophrenia at a dose of 1 tablet.

EXAMPLE 16

Soft gelatin capsules for oral use, each containing 10 mg of 8-chloro-1-methyl-6-phenyl-4H-s-triazolo[4,3-a][1,4]benzodiazepine are prepared by first dispersing the micronized compound in corn oil to render the material capsulatable and then encapsulating in the usual manner.

One capsule taken daily is useful to treat the negative symptoms of schizophrenia.

EXAMPLE 17

One thousand tablets, each containing 5 mg. of 8-chloro-1-methyl- 6-phenyl-4H-s-triazolo[4,3-a][1,4]benzodiazepine are made from the following types and amounts of ingredients:

| | |
|---|---|
| 8-Chloro-1-methyl-6-phenyl-4H—s-triazolo[4,3-a][1,4]benzodiazepine | 5 Gm |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to treat the negative symptoms of schizophrenia at a dose of one tablet twice a day.

EXAMPLE 18

A sterile preparation suitable for intramuscular injection and containing 1 mg of 8-chloro-1-methyl-6-phenyl-4H-s-triazolo[4,3-a][1,4]benzodiazepine in each milliliter is prepared from the following ingredients:

| | |
|---|---|
| 8-Chloro-1-methyl-6-phenyl-4H—s-triazolo[4,3-a][1,4]benzodiazepine | 1 Gm |
| Benzyl benzoate | 200 ml |
| Methylparaben | 1.5 Gm |
| Propylparaben | 0.5 Gm |
| Cottonseed oil, q.s. | 1,000 ml |

One milliliter of this sterile preparation is injected to treat the negative symptoms of schizophrenia.

EXAMPLE 19

A lot of 10,000 tablets, each containing 0.5 mg of 8-chloro-1-hydroxymethyl-6-phenyl-4H-s-triazolo[4,3-a][1,4]benzodiazepine is prepared from the following types and amounts of ingredients:

| | |
|---|---|
| 8-Chloro-1-hydroxymethyl-6-phenyl-4H—s-triazolo[4,3-a][1,4]benzodiazepine | 5 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in treating the negative symptoms of schizophrenia at a dose of 4 tablets 4 times a day.

EXAMPLE 20

One thousand two-piece hard gelatin capsules, each containing 2 mg of 8-chloro-1-hydroxymethyl-6-phenyl-4H-s-triazolo[4,3-a][1,4]benzodiazepine are prepared from the following types and amounts of ingredients:

| | |
|---|---|
| 8-Chloro-1-hydroxymethyl-6-phenyl-4H—s-triazolo[4,3-a][1,4]benzodiazepine | 2. Gm |
| Talc | 25 Gm |
| Lactose | 250 Gm |

The ingredients are mixed well and filled into capsules of the proper size.

Capsules so prepared are useful to treat the negative symptoms of schizophrenia at a dose of one capsule four times a day.

EXAMPLE 21

One thousand tablets for sublingual use are prepared from the following ingredients:

| | |
|---|---|
| 8-Chloro-1-hydroxymethyl-6-phenyl-4H—s-triazolo[4,3-a][1,4]benzodiazepine | 5 Gm |
| Polyethylene glycol 4,000, powdered | 150 Gm |
| Polyethylene glycol 6,000, powdered | 75 Gm |

The ingredients are mixed well and compresed into sublingual-type tablets weighing 230 mg.

These tablets placed under the tongue are useful in treating the negative symptoms of schizophrenia at a dose of one tablet.

EXAMPLE 22

Soft gelatin capsules for oral use, each containing 10 mg of 8-chloro-1-hydroxymethyl-6-phenyl-4H-s-triazolo[4,3-a][1,4]benzodiazepine are prepared by first dispersing the micronized compound in corn oil to render the material capsulatable and then encapsulating in the usual manner.

One capsule taken daily is useful to treat the negative symptoms of schizophrenia.

EXAMPLE 23

One thousand tablets, each containing 10 mg of 8-chloro-1-hydroxymethyl-6-phenyl-4H-s-triazolo[4,3-a][1,4]benzodiazepine are made from the following types and amounts of ingredients:

| | |
|---|---|
| 8-Chloro-1-hydroxymethyl-6-phenyl-4H—s-triazolo[4,3-a][1,4]benzodiazepine | 10 Gm |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to treat the negative symptoms of schizophrenia at a dose of one tablet twice a day.

EXAMPLE 24

A sterile preparation suitable for intramuscular injection and containing 2 mg of 8-chloro-1-hydroxymethyl-6-phenyl-4H-s-triazolo-[4,3-a][1,4]benzodiazepine in each milliliter is prepared from the following ingredients:

| | |
|---|---|
| 8-Chloro-1-hydroxymethyl-6-phenyl-4H—s-triazolo[4,3-a][1,4]benzodiazepine | 2 Gm |
| Benzyl benzoate | 200 ml |
| Methylparaben | 1.5 Gm |
| Propylparaben | 0.5 Gm |
| Cottonseed oil, q.s. | 1,000 ml |

One milliliter of this sterile preparation is injected to treat the negative symptoms of schizophrenia.

EXAMPLE 25

Following the procedure of the preceding Examples 19 through 24, inclusive, compositions are similarly prepared and administered substituting an equal amount of the 1-methyl, ethyl or propyl ether, the 1-acetate, propionate or hemisuccinate ester of the compound of the examples.

EXAMPLE 26

A lot of 10,000 tablets, each containing 0.5 mg of 1-methyl-8-chloro-6-(o-chlorophenyl)-4H-s-triazolo[4,3-a][1,4]benzodiazepine is prepared from the following types and amounts of ingredients:

| | |
|---|---|
| 1-Methyl-8-chloro-6-(o-chlorophenyl)-4H—s-triazolo[4,3-a][1,4]benzodiazepine | 1 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in treating the negative symptoms of schizophrenia at a dose of 1 tablet 4 times a day.

EXAMPLE 27

One thousand two-piece hard gelatin capsules, each containing 0.5 mg of 1-methyl-8-chloro-6-(o-chlorophenyl)-4H-s-triazolo[4,3-a][1,4]benzodiazepine are prepared from the following types and amounts of ingredients:

| | |
|---|---|
| 1-Methyl-8-chloro-6-(o-chlorophenyl)-4H—s-triazolo[4,3-a][1,4]benzodiazepine | 0.5 Gm |
| Talc | 25 Gm |
| Magnesium stearate | 250 Gm |

The ingredients are mixed well and filled into capsules of the proper size.

Capsules so prepared are useful to treat the negative symptoms of schizophrenia at a dose of one capsule four times a day.

EXAMPLE 28

One thousand tablets for sublinqual use are prepared from the following ingredients:

| | |
|---|---|
| 1-Methyl-8-chloro-6-(o-chlorophenyl)-4H—s-triazolo[4,3-a][1,4]benzodiazepine | 1 Gm |
| Polyethylene glycol 4,000, powdered | 150 Gm |
| Polyethylene glycol 6,000, powdered | 75 Gm |

The ingredients are mixed well and compressed into sublingual-type tablets weighing 226 mg.

These tablets placed under the tongue are useful in treating the negative symptoms of schizophrenia at a dose of 1 tablet.

EXAMPLE 29

Soft gelatin capsules for oral use, each containing 10 mg of 1-methyl- 8-chloro-6-(o-chlorophenyl)-4H-s-triazolo[4,3-a][1,4]benzodiazepine are prepared by first dispersing the micronized compound in corn oil to render the material capsulatable and then encapsulating in the usual manner.

One capsule taken daily is useful to treat the negative symptoms of schizophrenia.

EXAMPLE 30

One thousand tablets, each containing 5 mg. of 1-methyl-8-chloro-6-(o-chlorophenyl)-4H-s-triazolo[4,3-a][1,4]benzodiazepine are made from the following types and amounts of ingredients:

| | |
|---|---|
| 1-Methyl-8-chloro-6-(o-chlorophenyl)-4H—s-triazolo[4,3-a][1,4]benzodiazepine | 5 Gm |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to treat the negative symptoms of schizophrenia at a dose of one tablet twice a day.

EXAMPLE 31

A sterile preparation suitable for intramuscular injection and containing 1 mg of 1-methyl-8-chloro-6-(o-chlorophenyl)-4H-s-triazolo-[4,3-a][1,4]benzodiazepine in each milliliter is prepared from the following ingredients:

| | |
|---|---|
| 1-Methyl-8-chloro-6-(o-chlorophenyl)-4H—s-triazolo[4,3-a][1,4]benzodiazepine | 1 Gm |
| Benzyl benzoate | 200 ml |
| Methylparaben | 1.5 Gm |
| Propylparaben | 0.5 Gm |
| Cottonseed oil, q.s. | 1,000 ml |

One milliliter of this sterile preparation is injected to treat the negative symptoms of schizophrenia.

EXAMPLE 32

Following the procedures of the preceding Examples 1 through 31, inclusive, compositions are similarly prepared and administered substituting an equal amount of the N-oxide or hydrochloride salt of the active compound of the examples.

EXAMPLE 33

A lot of 1,000 tablets, each containing 1.0 mg of 8-chloro-1-methyl-6-phenyl-4H-s-triazolo[4,3-a][1,4]benzodiazepine is prepared from the following types and amounts of ingredients:

| | |
|---|---|
| 8-Chloro-1-methyl-6-phenyl-4H—s-triazolo[4,3-a][1,4]benzodiazepine | 1 Gm |
| Dicalcium phosphate | 1,500 Gm |
| Methylcellulose, U.S.P. (15 cps.) | 60 Gm |
| Talc | 150 Gm |
| Corn Starch | 200 Gm |
| Calcium stearate | 12 Gm |

The compound and dicalcium phosphate are mixed well, granulated with 7.5 percent solution of methylcellulose in water, passed through a No. 8 screen and dried carefully. The dried granules are passed through a No. 12 screen, mixed thoroughly with the talc, starch and stearate, and compressed into tablets.

These tablets are useful in treating the negative symptoms of schizophrenia in an adult human at a dose of 5 tablets per day in divided doses (one tablet at 7:00 a.m. and 3:00 p.m., three tablets at bedtime).

EXAMPLE 34

Soft gelatin capsules for oral use, each containing 2 mg of 8-chloro-1-methyl-6-phenyl-4H-s-triazolo[4,3-a][1,4]benzodiazepine are prepared by first dispersing the micronized compound in corn oil to render the material capsulatable and then encapsulating in the usual manner.

Four capsules taken daily in divided doses are useful to treat the negative symptoms of schizophrenia in an adult human, one capsule in the morning and mid-afternoon and two capsules at bedtime.

EXAMPLE 35

One thousand tablets, each containing 3 mg. of 8-chloro-1-methyl-6-phenyl-4H-s-triazolo[4,3-a][1,4]benzodiazepine are made from the following types and amounts of ingredients:

| | |
|---|---|
| 8-Chloro-1-methyl-6-phenyl-4H—s-triazolo[4,3-a][1,4]benzodiazepine | 3 Gm |
| Lactose | 355 Gm |
| Microcrystalline cellulose NF | 120 Gm |
| Starch | 16 Gm |
| Magnesium stearate powder | 4 Gm |

The ingredients are screened and blended together and pressed into 500 mg tablets.

The tablets are useful to treat the negative symptoms of schizophrenia in an adult human at a dose of one tablet three times per day.

EXAMPLE 36

A sterile preparation suitable for intramuscular injection and containing 1 mg of 8-chloro-1-methyl-6-phenyl-4H-s-triazolo[4,3-a][1,4]benzodiazepine in each milliliter is prepared from the following ingredients:

| | |
|---|---|
| 8-Chloro-1-methyl-6-phenyl-4H—s-triazolo[4,3-a][1,4]benzodiazepine | 1 Gm |

| | |
|---|---|
| Benzyl benzoate | 200 ml |
| Methylparaben | 1.5 Gm |
| Propylparaben | 0.5 Gm |
| Cottonseed oil, q.s. | 1,000 ml |

Five milliliters of this sterile preparation are injected in divided doses to treat the negative symptoms of schizophrenia in an adult human.

I claim:

1. A process for preventing or treating the negative symptoms of schizophrenia comprising the administration to a human subject in need of such treatment, in unit dosage form, from about 0.01 mg to about 0.8 mg/kg body weight of a compound of the formula:

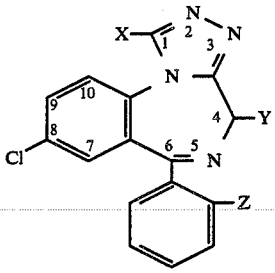

X is a member selected from the group consisting of —H, —CH₃, and —CH₂—O—R;
wherein R is hydrogen, alkyl of from 1 to 3 carbon atoms, inclusive

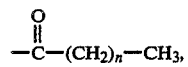

or

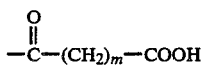

wherein n is 0 to 16, inclusive, and m is 1 to 16, inclusive;
Y is hydrogen or, provided when Z is hydrogen and X is CH₃, hydroxy;
Z is hydrogen or, provided when Y is hydrogen and X is —CH₃, chloro;
or the pharmacologically acceptable acid addition salt or a (5) N-oxide thereof in association with a pharmaceutical carrier.

2. A process of claim 1 wherein from about 0.02 mg to about 0.8 mg/kg body weight of a compound of the formula:

Formula I

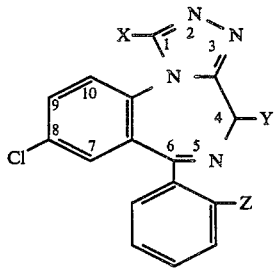

wherein X is a group consisting of —CH₂—O—R; wherein wherein R is hydrogen, alkyl of from 1 to 3 carbon atoms, inclusive

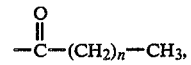

or

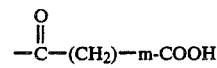

wherein n is 0 to 16, inclusive, and m is 1 to 16, inclusive; or the pharmacologically acceptable acid addition salt or a (5) N-oxide thereof in association with a pharmaceutical carrier is utilized.

3. The process of claim 2 wherein the compound is 8-chloro-1-hydroxymethyl-6-phenyl-4H-s-triazolo[4,3-a][1,4]benzodiazepine.

4. The process of claim 2 wherein the compound is an acid addition salt of 8-chloro-1-hydroxymethyl-6-phenyl-4H-s-triazolo[4,3-a][1,4]benzodiazepine.

5. The process according to claim 1 wherein from about 0.01 mg to about 0.4 mg/kg body weight of 8-chloro-6-phenyl-4H-s-triazolo-[4,3-a][1,4]benzodiazepine or the pharmacologically acceptable acid addition salt or a (5) N-oxide thereof in association with a pharmaceutical carrier is utilized.

6. The process of claim 5 wherein the 8-chloro-6-phenyl-4H-s-triazolo[4,3-a][1,4]benzodiazepine is in the form of the (5) N-oxide.

7. The process of claim 5 wherein the 8-chloro-6-phenyl-4H-s-triazolo[4,3-a][1,4]benzodiazepine is in the form of the free base.

8. The process according to claim 1 wherein from about 0.01 mg to about 0.4 mg/kg body weight of 1-methyl-8-chloro-6-phenyl-4H-s-triazolo[4,3-a][1,4]benzodiazepine or the pharmacologically acceptable acid addition salt or a (5) N-oxide thereof in association with a pharmaceutical carrier is utilized.

9. The process of claim 8 wherein the 1-methyl-8-chloro-6-phenyl-4H-s-triazolo[4,3-a][1,4]benzodiazepine is in the form of the (5) N-oxide.

10. The process of claim 8 wherein the 1-methyl-8-chloro-6-phenyl-4H-s-triazolo[4,3-a][1,4]benzodiazepine is in the form of the free base.

11. The process according to claim 1 wherein from about 0.01 mg to about 0.4 mg/kg body weight of 1-methyl-4-hydroxy-8-chloro-6-phenyl-4H-s-triazolo[4,3-a][1,4]benzodiazepine or the pharmacologically acceptable acid addition salt or a (5) N-oxide thereof in association with a pharmaceutical carrier is utilized.

12. The process of claim 11 wherein the 1-methyl-4-hydroxy-8-chloro-6-phenyl-4H-s-triazolo[4,3-a][1,4]benzodiazepine is in the form of the (5) N-oxide.

13. The process of claim 11 wherein the 1-methyl-4-hydroxy-8-chloro-6-phenyl-4H-s-triazolo[4,3-a][1,4]benzodiazepine is in the form of the free base.

14. The process according to claim 1 wherein from about 0.01 mg to about 0.4 mg/kg body weight of 1-methyl-8-chloro-6-(o-chlorophenyl)4H-s-triazolo[4,3-a][1,4]benzodiazepine or the pharmacologically acceptable acid addition salt or a (5) N-oxide thereof in association with a pharmaceutical carrier is utilized.

15. The process of claim 14 wherein the 1-methyl-8-chloro-6-(o-chlorophenyl)-4H-s-triazolo[4,3-a][1,4]benzodiazepine is in the form of the (5) N-oxide.

16. The process of claim 14 wherein the 1-methyl-8-chloro-6-(o-chlorophenyl)-4H-s-triazolo[4,3-a][1,4]benzodiazepine is in the form of the free base.

17. A process for preventing or treating the negative symptoms of schizophrenia comprising the administration to an adult human subject, in unit dosage form, of from about 5 mg to about 10 mg/day of 1-methyl-8-chloro-6-phenyl-4H-s-triazolo[4,3-a][1,4]benzodiazepine or the pharmacologically acceptable acid addition salt or a (5) N-oxide thereof in association with a pharmaceutical carrier.

18. The process of claim 17 where the 1-methyl-8-chloro-6-phenyl-4H-s-triazolo[4,3-a][1,4]benzodiazepine is in the form of the free base.